United States Patent
West et al.

(10) Patent No.: US 8,691,765 B2
(45) Date of Patent: Apr. 8, 2014

(54) METALLOTHIONEIN BASED NEURONAL THERAPEUTIC AND THERAPEUTIC METHODS

(75) Inventors: Adrian Keith West, Lenah Valley (AU); Meng Inn Chuah, Sandy Bay (AU); James Clement Vickers, Newtown (AU); Roger Steven Chung, Sandy Bay (AU)

(73) Assignee: University of Tasmania, Tasmania (AU)

( * ) Notice: Subject to any disclaimer, the term of this patent is extended or adjusted under 35 U.S.C. 154(b) by 1534 days.

(21) Appl. No.: 10/517,653

(22) PCT Filed: Jun. 13, 2003

(86) PCT No.: PCT/AU03/00735
§ 371 (c)(1),
(2), (4) Date: Mar. 8, 2005

(87) PCT Pub. No.: WO03/105910
PCT Pub. Date: Dec. 24, 2003

(65) Prior Publication Data
US 2005/0130888 A1 Jun. 16, 2005

Related U.S. Application Data

(60) Provisional application No. 60/584,671, filed on Jul. 2, 2004.

(30) Foreign Application Priority Data

Jun. 13, 2002 (AU) .................................. PS 2958

(51) Int. Cl.
*A61K 38/17* (2006.01)
*A61P 25/06* (2006.01)

(52) U.S. Cl.
USPC .......... 514/12.4; 514/1.1; 514/17.7; 514/17.8; 514/18.2; 514/18.9

(58) Field of Classification Search
None
See application file for complete search history.

(56) References Cited

U.S. PATENT DOCUMENTS

| 5,268,175 A | 12/1993 | Bombardelli et al. |
| 5,431,923 A | 7/1995 | Bombardelli et al. |
| 2002/0155170 A1* | 10/2002 | Walsh et al. .................. 424/643 |

FOREIGN PATENT DOCUMENTS

| FR | 2 813 529 | 3/2002 | |
| WO | WO 98/31795 A | 7/1998 | |
| WO | WO 02/43507 A | 6/2002 | |
| WO | 03/035033 * | 5/2003 | ............. A61K 9/127 |

OTHER PUBLICATIONS

Ebadi et al. 1998. Restorative Neurology and Neuroscience 12(2-3):103-111.*
Penkowa 2002. Journal of Comparative Neurology 444:174-189.*
Garrett 2000. The Prostate 43:125-135.*
Sigma catalog, M9542, printed Aug. 22, 2007.*
Asanuma 2002. Neuroscience Letters 327:61-65.*

(Continued)

*Primary Examiner* — Daniel E Kolker
*Assistant Examiner* — Aurora M Fontainhas
(74) *Attorney, Agent, or Firm* — Knobbe, Martens, Olson & Bear, LLP

(57) ABSTRACT

A method of stimulating neuronal growth or repair comprising exposing a target neuron or neuronal area to a solution of the metallothionein isoform MT-IIA.

21 Claims, 20 Drawing Sheets

(56) References Cited

OTHER PUBLICATIONS

Fry 2001. Clinical and Experimental Pharmacology and Physiology 28:253-258.*
Schwob 2002. The Anatomical Record (New Anat.) 269:33-49.*
Deguchi 2000 (Pharmaceutical Research 17(1):63-69).*
Yoshimura 2001 (Proc Natl Acad Sci USA 98(10):5874-5879).*
van Lookeren Campagne et al. 1999 Proc Natl Acad Sci USA 96:12870-12875.*
Richarz, A.N., et al.; "Speciation Analysis of Trace Elements in the Brains of Individuals with Alzheimer's Disease with Special Emphasis on Metallothioneins"; *Anal Bioanal Chem.*; vol. 372(3); pp. 412-417 (2002).
Lui, E., et al; "Metals and the Liver in Alzheimer's Disease: An Investigation of Hepatic Zinc, Copper, Cadmium, and Metallothionein"; *J. Am. Geriatr Soc*; vol. 38(6); pp. 633-639 (1990).
Aldard, P.A., et al; "Increased Density of Metallothionein I/II-Immunopositive Cortical Glial Cells in the Early Stages of Alzheimer's Disease"; *Neurobiology of Disease*; vol. 5(5); pp. 349-356 (1998).
Zambenedetti, P., et al; "Metallothioneins are Highly Expressed in Astrocytes and Microcapillaries in Alzheimer's Disease"; *Journal of Chemical Neuroanatomy*; vol. 15(1); pp. 21-26 (1998).
Aschner, M., "The Functional Significance of Brain Metallothioneins"; *The FASEB Journal*; vol. 10(10); pp. 1129-1136 (1996).
Penkowa, M. et al., Metallothionein treatment reduces proinflammatory cytokines IL-6 and TNF-alpha and apoptotic cell death during experimental autoimmune encephalomyelitis (EAE), Experimental Neurology, Jul. 2001, vol. 170, No. 1, pp. 1-14.
Ambjørn et al., "Metallothionein and a peptide modeled after metallothionein, EmtinB, induce neuronal differentiation and survival through binding to receptors of the low-density lipoprotein receptor family," Journal of Neurochemistry, 2008, vol. 104, pp. 21-37.
Benn and Woolf, "Adult neuron survival strategies—slamming on the brakes," Nature Reviews Neuroscience, Sep. 2004, vol. 5, pp. 686-700.
Chung et al., "Redefining the role of metallothionein within the injured brain," The Journal of Biological Chemistry, May 30, 2008, vol. 283, No. 22, pp. 15349-15358.
Chung et al., "Metallothionein-IIA promotes initial neurite elongation and postinjury reactive neurite growth and facilitates healing after focal cortical brain injury," The Journal of Neuroscience, Apr. 15, 2003, vol. 23(8), pp. 3336-3342.
Fitzgerald et al., "Metallothionein-IIA promotes neurite growth via the megalin receptor," Exp. Brain Res., 2007, vol. 183, pp. 171-180.
Køhler et al., "The role of metallothionein II in neuronal differentiation and survival," Brain Research, 2003, vol. 992, pp. 128-136.
Penkowa et al., "CNS wound healing is severely depressed in metallothionein I- and II-deficient mice," The Journal of Neuroscience, Apr. 1, 1999, vol. 19(7), pp. 2535-2545.
Penkowa et al., "Metallothionein reduces central nervous system inflammation, neurodegeneration, and cell death following kainic acid-induced epileptic seizures," Journal of Neuroscience Research, 2005, vol. 79, pp. 522-534.
Okada et al., "Synthesis of a nonacosapeptide (beta-fragment) corresponding to the N-terminal sequence 1-29 of human liver metallothionein II and its heavy metal-binding properties," FEBS 2483, Apr. 1985, vol. 183(2), pp. 375-378.
Sewell et al., "Bioactivity of Metallothionein-3 correlates with its novel beta domain sequence rather than metal binding properties." Biochemistry 1995, vol. 34, pp. 4740-4747.
Siddiq and Filbin, "Metallothionein I/II can overcome MAG and myelin-mediated inhibition," Neuroscience 2005 Abstract, 2005.

* cited by examiner

GAP-43 labelled axons in proximal optic nerve

PBS injected

MT-I/II injected

METALLOTHIONEIN BASED NEURONAL THERAPEUTIC AND THERAPEUTIC METHODS

This application is the U.S. National Phase of International Application PCT/AU03/00735, filed 13 Jun. 2003, which designated the U.S. PCT/AU03/00735 claims priority to Australian Application No. PS 2958 filed 13 Jun. 2002, which claims priority to application 60/584,671, filed 7 Feb. 2004. The entire content of these applications are incorporated herein by reference.

INTRODUCTION TO THE INVENTION

This invention relates to the use of metallothionein as an active ingredient in effecting and enhancing recovery of damaged neuronal tissue, particularly following physical trauma and damage thereto. The invention provides a therapeutic incorporating metallothionein and methods of treatment based thereon.

BACKGROUND TO THE INVENTION

Metallothionein (MT) is a naturally occurring peptide, which is present in most cells of the mammalian body. There are many isoforms in humans, but these resolve into four classes; MT-I and MT-II which are expressed widely, MT-III which is mainly found in the brain, and MT-IV which is restricted to specific epithelial sites. MTs are intracellular proteins with occasional nuclear localisation, and although there are persistent reports of extracellular detection of MT, the prevailing dogma is fixed that their physiological role is within cells.

MTs are metal binding proteins (61-68 amino acids), which normally bind seven zinc ions, although zinc/copper mixtures have been reported. Some isoforms are rapidly induced in response to increases in zinc or copper levels, and also by a large number of hormones and cytokines, including glucocorticoids, interleukin 1 and 6, interferons and so on. Their exact physiological role is unclear. Early suggestions that they act to prevent accumulation of toxic levels of heavy metals are no longer favoured, and if their role is indeed in metal metabolism, it is more likely that they are involved in the intracellular homeostasis of zinc. However, MTs are efficient scavengers of free radicals and are able to protect DNA and other molecules from oxidation, suggesting that their function may be protective. MTs may be considered intracellular stress proteins which respond to a wide variety of stimuli.

It is relevant that MT-I/II knockout animals, and those which overexpress MT-I and MT-II are phenotypically normal, except for sensitivity and resistance, respectively, to some chemical and physical stresses.

Deficiency of MT-III, the "brain-specific" class of MT, has been implicated in the pathogenesis of Alzheimer's disease, although this finding has been strongly disputed. MT-III reduces neuronal survival, and the applicants have shown that, when MT-III is added to cultured neurons it reduces neurite sprouting. Exogenous MT-III appears to have an opposing effect to MT-IIA and it is expected that comparison of their structures will reveal strategies for designing analogues of both which have specific neurotrophic properties. It has been shown that exposure of rat brain lesions to MT-III causes vacuolisation, consistent with extensive neuronal death.

Metallothionein and Heavy Metals

There is a large body of literature on the relationship between metallothionein and heavy metals, particularly cadmium. MT was originally isolated as a cadmium-binding protein, and it is known that it acts as the major intracellular sink for this toxic metal. Hence, people exposed to cadmium in the workplace or through contaminated diet will have elevated metallothionein levels, particularly in the kidney. There is no question that MT acts to protect cells against cadmium, however it is not an effective agent, nor is it likely that this is the actual physiological role for the protein: it is likely an adventitious property derived from the chemical similarity between zinc and cadmium. One consequence of this is the numerous studies of the pharmacokinetics of metallothionein bound to heavy metals, following various routes of administration. Whilst cadmiummetallothionein is (not surprisingly) toxic, it is not believed that zinc or copper-metallothioneins will have significant metal-based toxicity at the concentrations employed in the studies below.

The applicants have examined the action of metallothionein proteins; including MT-IIA, a major human metallothionein of the MT-I/II class. The studies found that administration of metallothionein to cultured rat neurons increases neuronal survival and enhances the rate of axonal extension. Furthermore, in lesioned rat brains, metallothionein enhances regenerative axonal extension into the lesions and replacement of damaged tissue. Accordingly, the use of metallothionein as an active ingredient in neuronal therapy provides a novel method of stimulating neuronal growth and neuronal survival, a novel class of therapeutic agents and a novel method of treatment for a range of neuronally based disease states.

Moreover, metallothionein offers several practical advantages as a therapeutic agent.

1. It is a naturally occurring, non-toxic protein
2. It appears possible that intraperitoneally administered metallothionein can enter the CNS compartment, following physical trauma to the brain or spinal cord or breakdown of the blood-brain barrier due to other causes.
3. Metallothionein is not post-translationally modified and hence can be easily produced in bacterial or other expression systems
4. Metallothionein is a small peptide (61 amino acids for MT-IIA, 68 amino acids for human MT-III) and it is very likely that a novel analogue which is amenable to chemical synthesis can be designed.

STATEMENT OF THE INVENTION

In one aspect the invention provides a method of stimulating neuronal growth comprising exposing a target neuron to metallothionein.

The target neuron is preferably placed in direct contact with a metallothionein solution.

The target neuron may have suffered physical trauma including lesion or other forms of neurodegeneration.

The metallothionein may be selected from any one or a combination of known metallothionein classes including MT-I, MT-II, MT-III and MT-IV and the associated isoforms.

Most preferably the metallothionein is selected from MT-II including human MT-IIA.

The metallothionein may be a synthetic analogue which combines structural or physical features of any or all known metallothionein isoforms.

The metallothionein may be provided in solution at a concentration of up to about 5 µg/ml in a neurologically acceptable carrier.

Administration of the metallothionein solution may include MT-IIA as the sole active ingredient. Alternatively, any one or a combination of the metallothionein classes and isoforms as detailed above may be used. Where combinations of metallothionein are used the different classes and isoforms may be combined in a single dose. Alternatively, the different classes may be administered sequentially.

The administration regime may include initial administration of a solution of MT-IIA followed by a subsequent administration of a solution of MT-III. The administration regime may be limited to MT-IIA alone as the active ingredient.

The method of the invention may be applied to a range of compromised neuronal states including diseased states and injuries.

In another aspect the invention provides a method of treatment of any one or a combination of Alzheimers, Parkinsons, Motor Neuron Diseases, head injury, comprising the administration to a patient of a therapeutic including metallothionein as previously described as an active ingredient wherein said therapeutic is applied or administered so as to directly interact with the site of neuronal compromise.

In another aspect the invention provides a therapeutic composition comprising metallothionein in any one or a combination of isoforms, or as a synthetic metallothionein comprising features of one or more isoforms, as an active ingredient in a pharmaceutically acceptable carrier wherein said carrier is adapted for topical administration to an area of neuronal compromise.

The composition may be adapted for direct topical application to exposed neurons or for administration to non-exposed neurons by indirect routes including intravenous or intraperitoneal administration, which result in accumulation of metallothionein in the compromised region of the brain or other part of the central nervous system.

DETAILED DESCRIPTION OF THE INVENTION

The action of MT-IIA (a major human metallothionein of the MT-I/-II class) in two distinct culture models of rat cortical neurons, and in a rat in vivo model of cortical damage was examined. In culture, it was found that administration of MT-IIA increases neuronal survival, and enhances the rate of axonal extension. In lesioned rat brains, it was found that MT-IIA enhances regenerative axonal growth into the lesion, and replacement of damaged tissue.

Metallothionein Action on Cultured Rat Cortical Neurons:

Culture Model 1: Rat cortical neurons (E18) were plated at low density in neurobasal medium +B27 supplement, including 150 μg/ml of a rat brain extract. Recombinant MT-IIA was produced (the major human metallothionein I/II isoform) in *E. coli* cultures and reconstituted as a zincthionein (7 moles zinc/mole protein).

Culture Model 2: Rat cortical neurons (E18) were plated at a higher density in Neurobasal medium +B27 supplement (but without brain extract) and cultured in vitro for 21 days, allowing the formation of neuronal clusters connected by fasciculated axonal bundles.

Rat Cortical Injury Model: Focal injuries were performed to the adult rat neocortex by insertion of a 25 gauge beveled needle into the Par 1 region of the rat somatosensory cortex to a depth of 1.5 mm into the brain.

The invention will now be described with reference to a selection of embodiments and examples and FIGS. 1 to 12.

EXAMPLE 1

Figure 1:
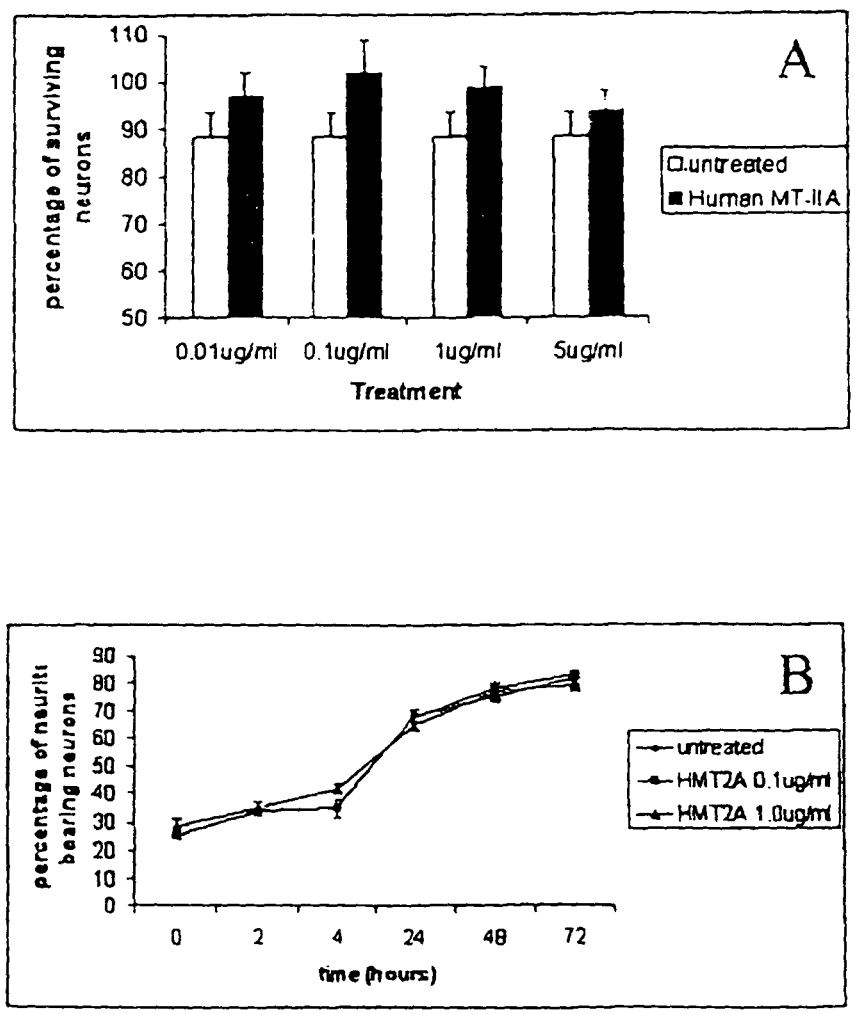
FIG. 1 shows some effects of human MT-IIA on neuronal survival and neurite elongation of cultured rat cortical neurons.
Figure 1:
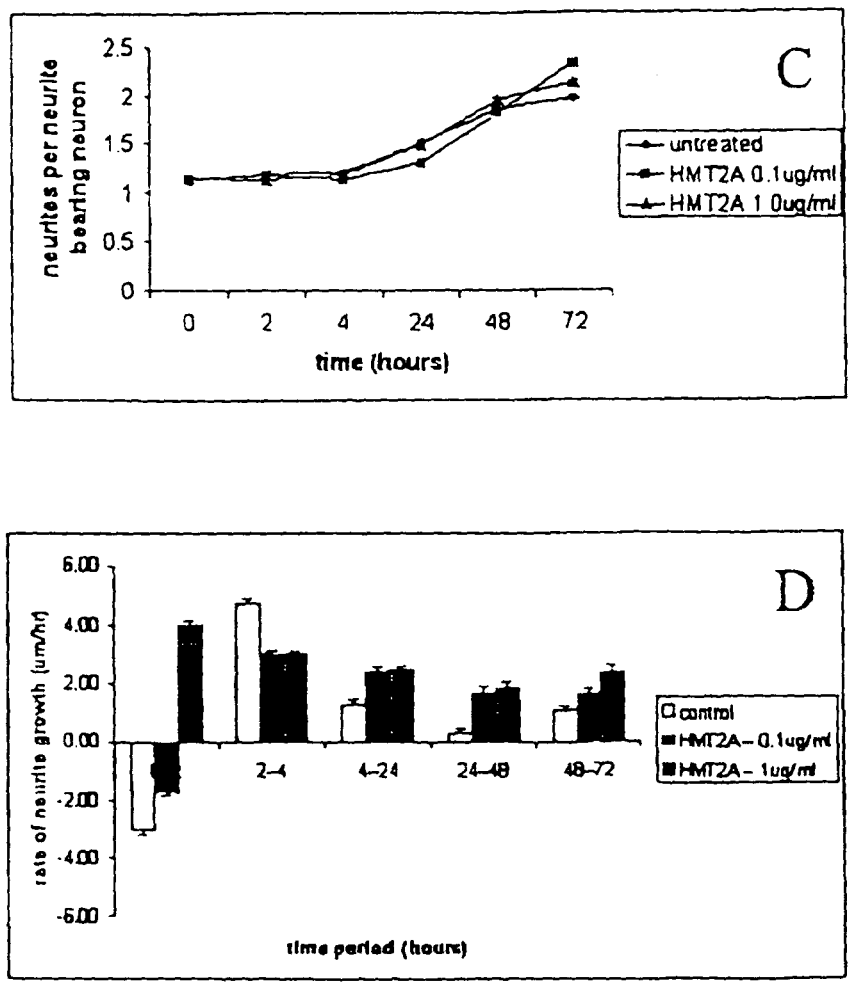

Referring in turn to FIGS. 1 to 7 a series of experiments were conducted using the composition made up of 0.1 to 5 μg/ml of MT-IIA in a pharmaceutically and neurologically acceptable carrier. Such a composition when applied topically to a range of in vivo and in vitro neuronal situations clearly demonstrates that MT-IIA functions as an active ingredient in enhancing neurite elongation. MT-IIA also dramatically increases the extension of processes between clusters following lesions formed by microscapel and ultimately demonstrates the ability of MT-IIA to have a dramatic effect on increasing the rate of recovery from physical injuries. Referring to FIG. 1, the bar graph in FIG. 1A demonstrates that human MT-IIA promotes neuronal survival in the presence of adult rat brain extract (150 μg/ml) after three days. ($P<0.01$, ANOVA). Accordingly Zn-MT is not detrimental to the survival of cultured neurons.

Referring now to FIGS. 6E and 6F, under the same conditions human MT-IIA does not increase the initiation of new neurite sprouting over three days, expressed as either the percentage of neurite bearing neurons as shown in FIG. 6E or the number of neurites per neurone as shown in FIG. 6F. $P>0.01$ ANOVA). This observation has important clinical ramifications as inappropriate sprouting of neurons has been associated with premature neuronal death.

Referring now to FIG. 7B the bar graph shows MT-IIA demonstrating dose dependent promotion of neurite elongation during this period. (P<0.01, ANOVA).

From the above experiments it has been demonstrated that MT-IIA is capable of enhancing neurite elongation of cultured rat cortical neurons without increasing the rate of undesirable neurite sprouting.

Figure 2:
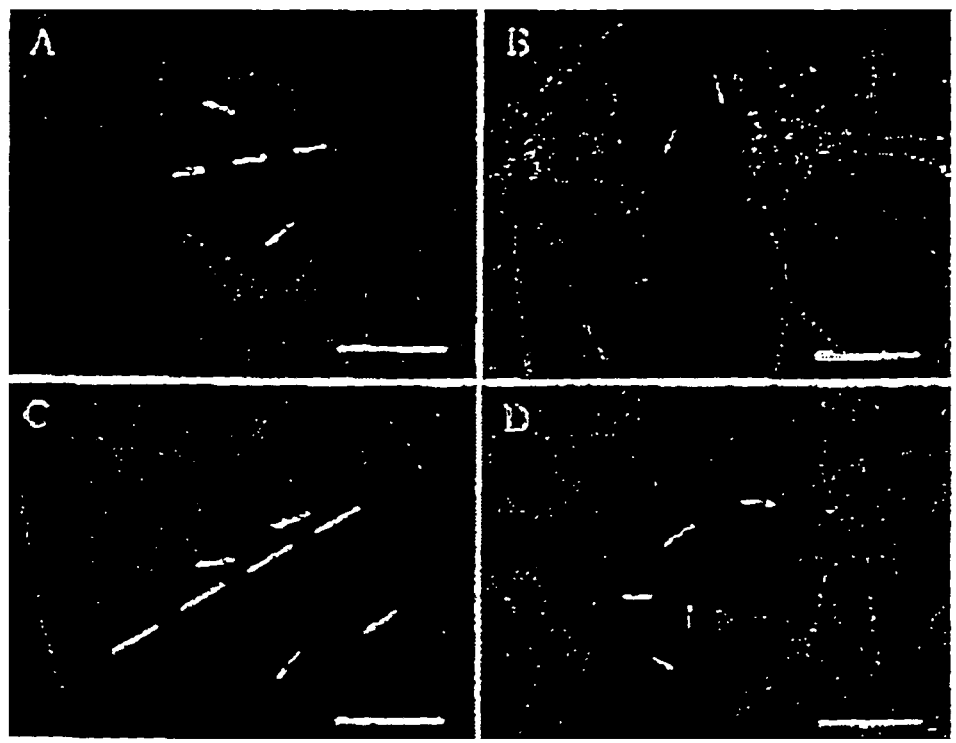
FIG. 2 shows by immunocytochemistry the effect of human MT-IIA on reactive neurite sprouting following axonal injury.

Referring now to FIG. 2 a culture of rat cortical neurons was maintained for twenty-one days in order to allow formation of clusters which are interconnected by fasciculated bundles of axons. The axons were cut with a microscapel and a composition as previously described, including recombinant MT-IIA, was added. The immunocytochemical results shown in FIGS. 2A to 2D show that twelve hours after cutting the neuronal bundles with a microscapel there is a marked retraction by transected neurites from the lesion site (which is indicated with a broken line) of up to 100 μm. Whilst in the absence of MT-IIA (FIG. 2A), there are very few neurite extensions, as assessed by NF-M immunoreactive processes (red) extending into the area of retraction (indicated by arrows) in untreated neurons, there are many in the MT-IIA treated neurons (FIG. 2C). Tau and βIII-tubulin immunocytochemical analysis also indicates very few processes extending into the area of retraction (indicated by arrows) in the absence of MT-IIA (FIG. 2B). However, after twelve hours of incubation with MT-IIA at a concentration of 1 μg/ml, these processes are significantly longer and have extended into the lesion site (FIG. 2D).

Figure 3:
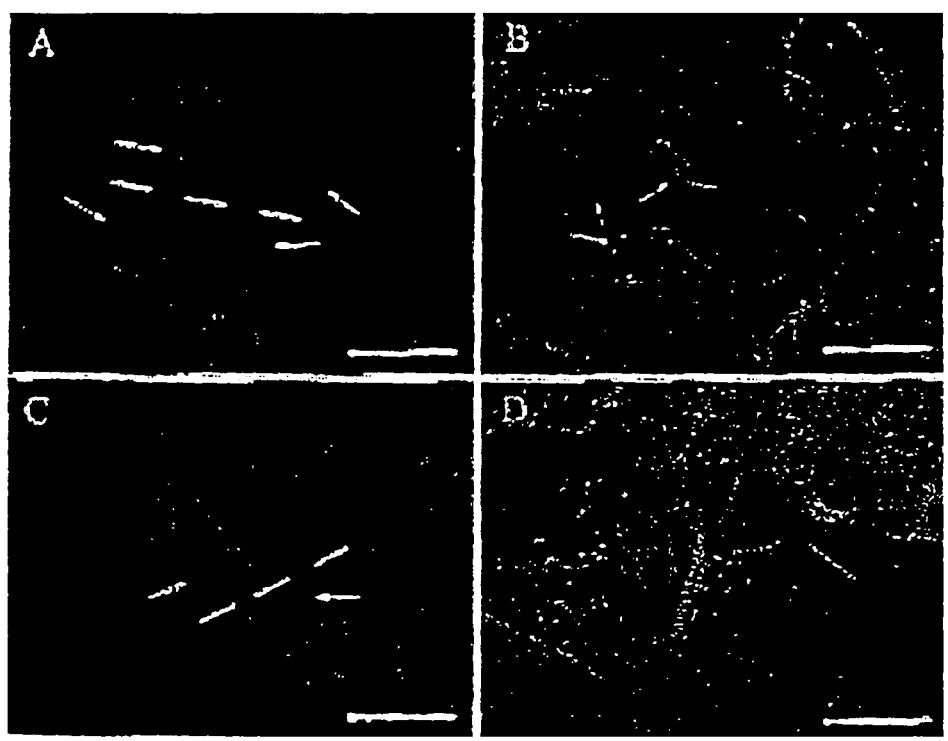
FIG. 3 shows by immunocytochemistry the effects of human MT-IIA on reactive neurite sprouting following axonal injury.

Referring now to FIG. 3 the experiments detailed in FIG. 2 were repeated with a longer exposure period of eighteen hours to recombinant MT-IIA. Eighteen hours after cutting the axonal bundles, the tissue was assessed by immunocytochemical markers and analysis of neurite extension into the lesion. In untreated samples, shown in FIG. 3A, there is minimal neurite growth into lesion site. However, as shown in FIG. 3C when a sample is treated with MT-IIA at a concentration of 1 μg/ml, the processes have completely traversed the lesion site with the immunoreactive processes shown in red extending from the neurite stumps indicated by arrows and have grown towards the central lesion site indicated by the broken line. From this experimental work it has been demonstrated that MT-IIA promotes growth of NF-M immunoreactive processes which are indicated by the arrows across the central lesion site. Tau and βIII-tubulin immunocytochemical analysis also indicates that a number of processes extend into the area of retraction indicated by arrows in untreated neurons. However, these processes do not cross the transection site shown in FIG. 3B. MT-IIA treated samples shown in FIG. 3D have been sufficiently promoted such that the growth of processes occurs and extends beyond the transection site indicated by arrows to the opposite stump of the transected neurite bundle.

Accordingly, these experiments clearly show that MT-IIA dramatically increases the extension of processes, including axons between clusters. This occurs following lesion by microscapel and after eighteen hours of exposure to MT-IIA the axonal bundles have bridged the region between the clusters. This effect of MT-IIA is a result of a direct topical interaction between the protein, the neurons and the culture medium.

Referring now to FIGS. 4, 5, 11 and 12 the action of MT-IIA on a rat model of cortical injury was investigated. The rat model of physical damage to the cortex has been previously developed by the inventors and extensively characterised in terms of neuronal damage, orthology, pathology and subsequent recovery.

FIGS. 4, 5, 11 and 12 show the extent of the physical injury, and microglial invasion of the cavity. MT-IIA administration reduced microglial infiltration and promoted formation of a tissue bridge across the lesion, from the pial surface down. MT-IIA also promoted axonal extension into the lesion site. Very few axonal extensions were seen in the rats treated with vehicle alone (control rats).

Figure 4:
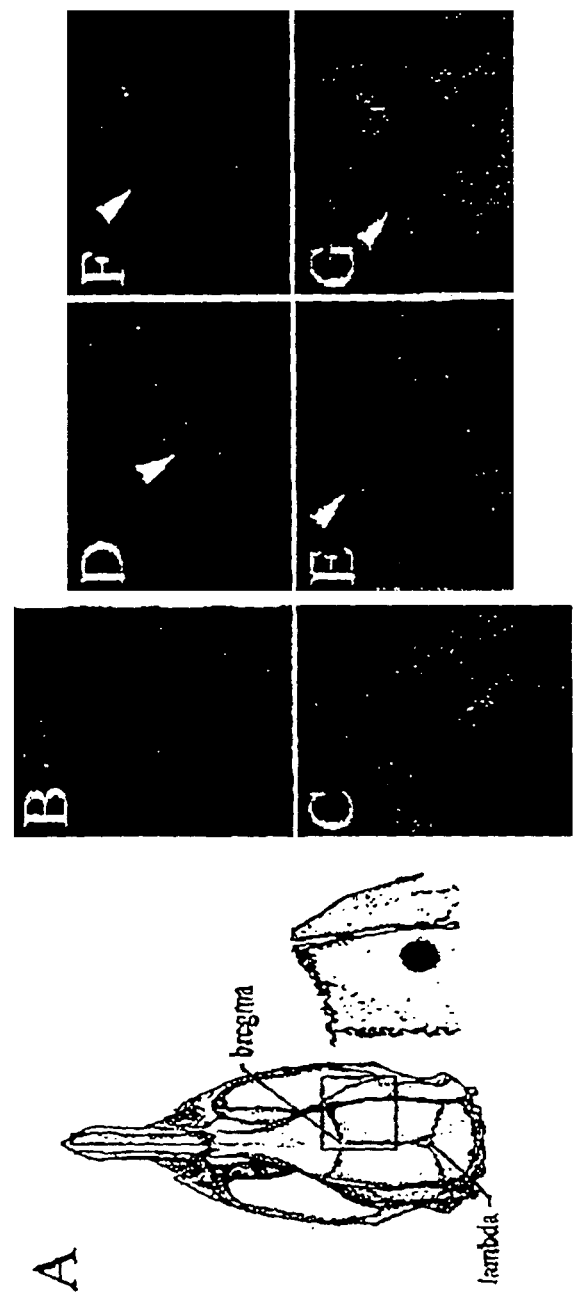
FIGS. 4 and 5 show the effect of human MT-IIA on lesions in the rat neocortex formed by physical injury.

FIG. 4 shows the global location of needle stick injuries as indicated in Panel A. Brain sections underwent immunohistochemistry against SMI-312 (green) and ferritin (red) 4 days post injury. Needle stick injury resulted in a large injury tract, and microglial migration into and surrounding the injury site (B). MT-IIA treatment reduced microglial infiltration, and promoted the formation of a tissue bridge enclosing the lesion site from the pial surface down, forming a teardrop like invagination (C). Microglia at the pial surface were small and round, in contrast to the large, amoeboid microglia observed in deeper cortical layers (D, E respectively). MT-IIA promoted regenerative axonal growth into the lesion site at both the pial layer (D) and deeper cortical layers (E). In contrast, very few axonal extensions were visualised in control rats, at the pial level (F) or deeper cortical layers (G). Arrowheads indicate the injury tract.

Figure 5:
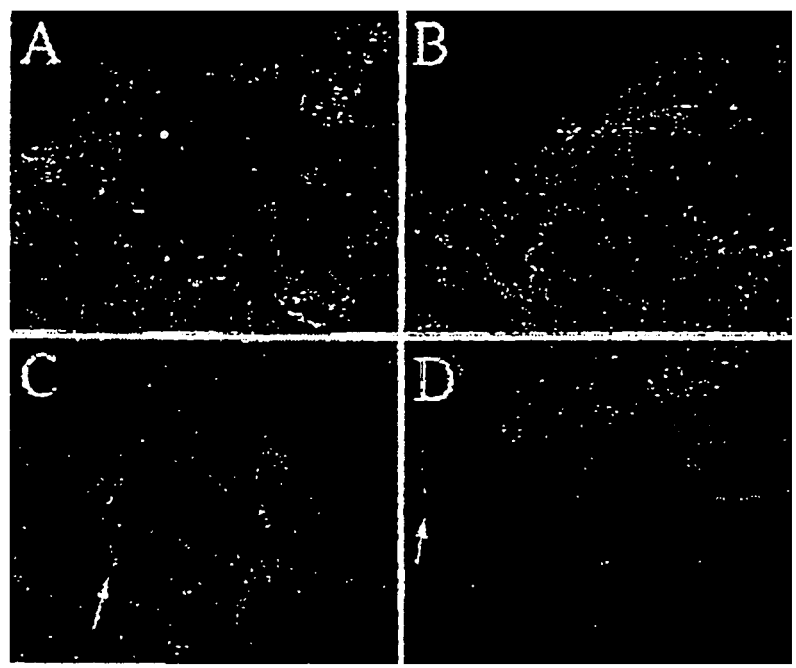

FIG. 5 shows immunohistochemical staining against SMI-312 (green) and ferritin (red) 4 days post injury. SMI-312 immunoreactive axonal extensions were often found in close association with small round microglia at the pial surface (A, B). Contrastingly, axonal extensions in deeper cortical layers were often not associated with larger, amoeboid microglia (C, D). Regenerating axons often exhibited a wavy morphology, as if they were constantly changing direction. Occasionally, pyramidal (indicated by arrow, C) and bulb-like (indicated by arrow, D) accumulations were observed along axonal sprouts.

The above experiments clearly indicated that the administration of recombinant MT-IIA dramatically increases the rate of recovery from physical injuries. In combination with the tissue culture experiments, this work indicates that the administration of MT-IIA following central nervous system injury acts directly on neurons to increase the rate of axonal extension into the lesion.

EXAMPLE 2

Figure 6:
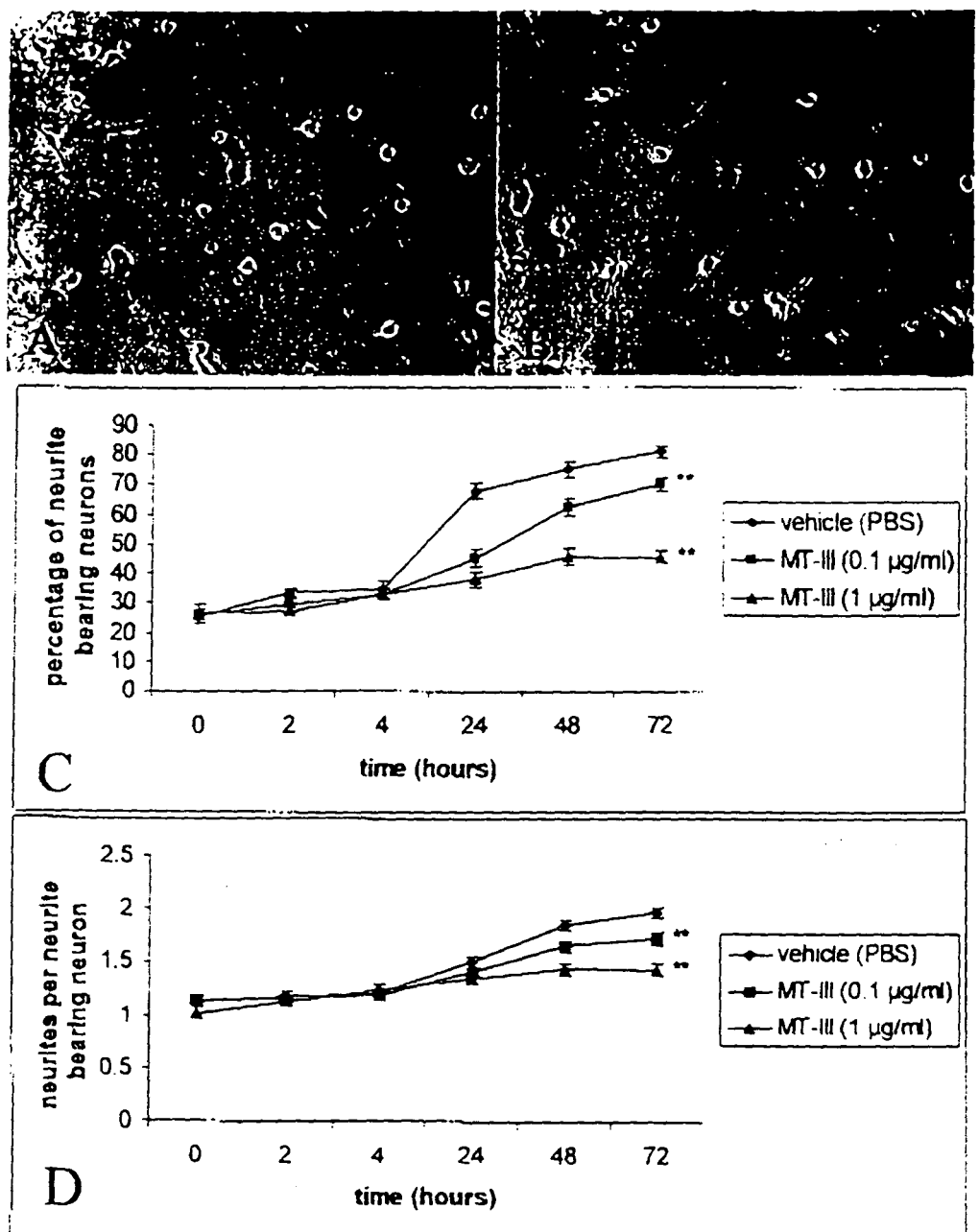
FIG. 6 shows the effect of human MT-III and MT-IIA on neurite formation and initial neurite outgrowth of cultured rat cortical neurons.
Figure 6:
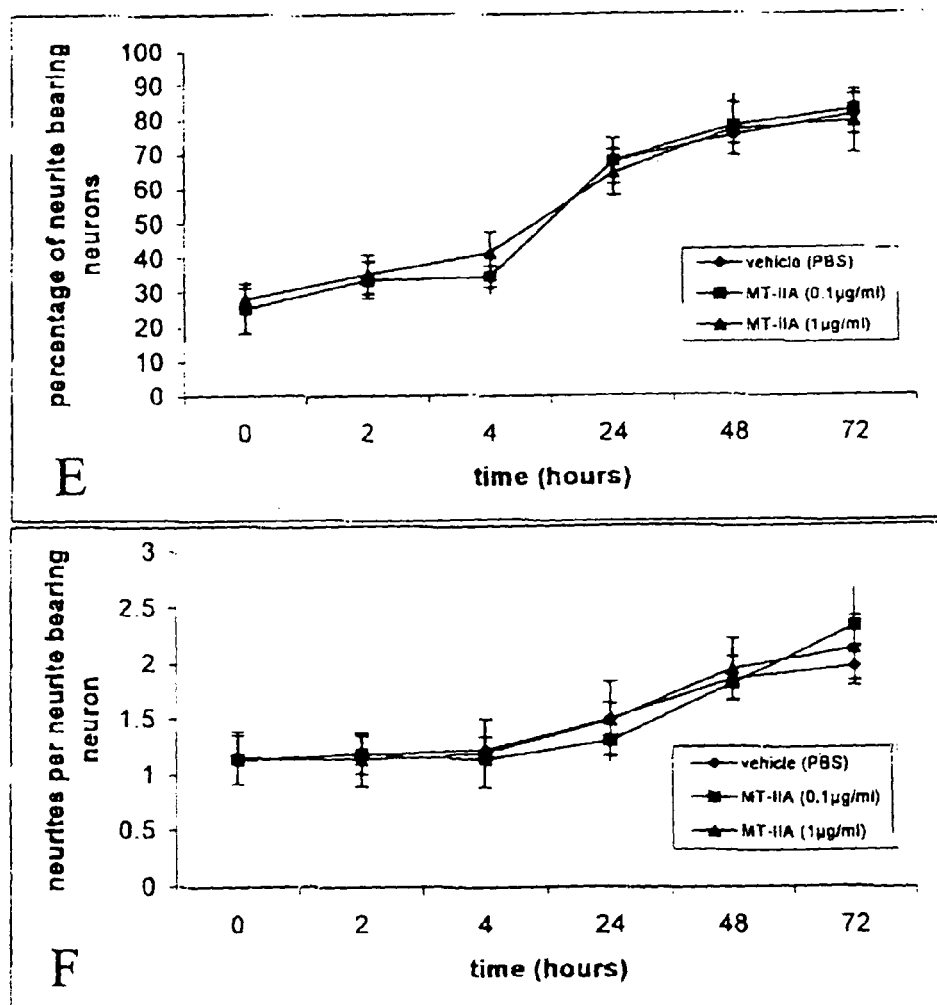
Figure 7:
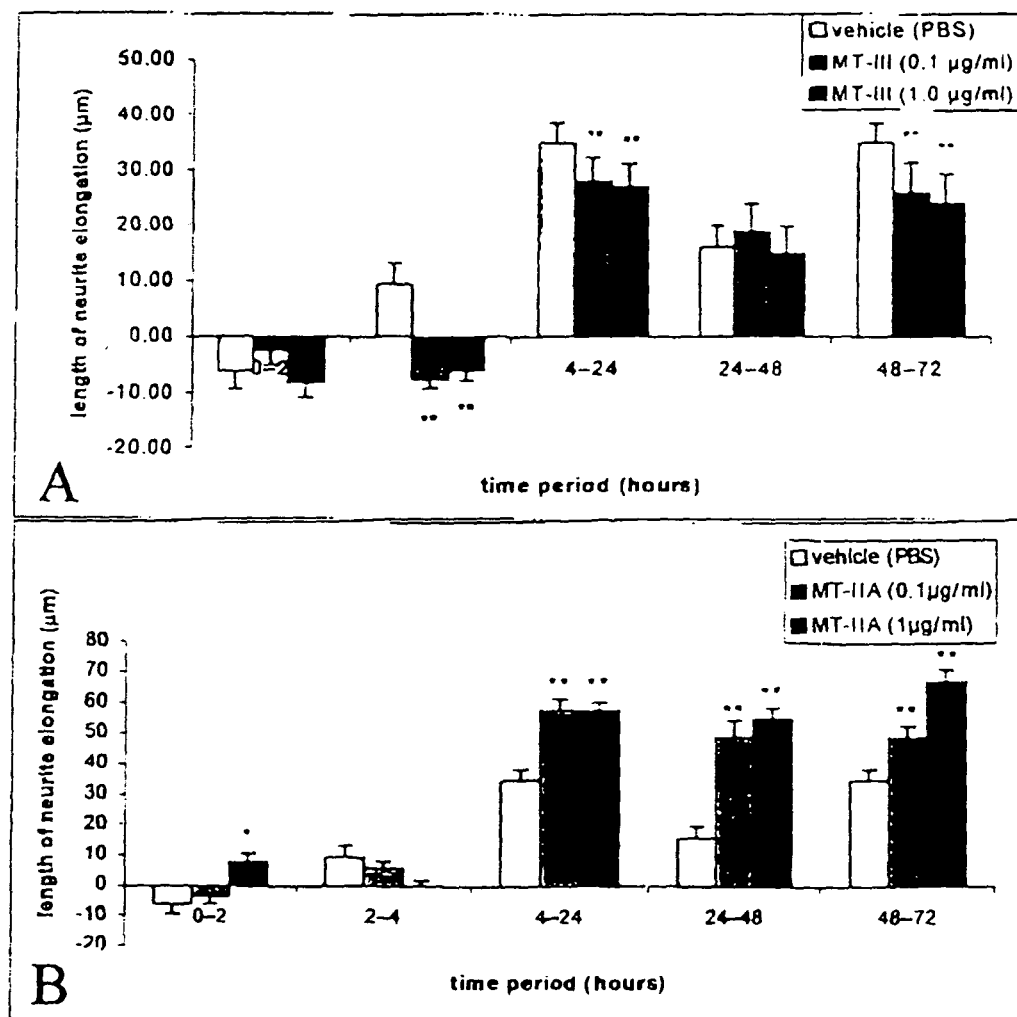
FIG. 7 shows the effect of human MT-III and MT-IIA on the extent and rate of neurite elongation of cultured rat cortical neurons.
Figure 8:
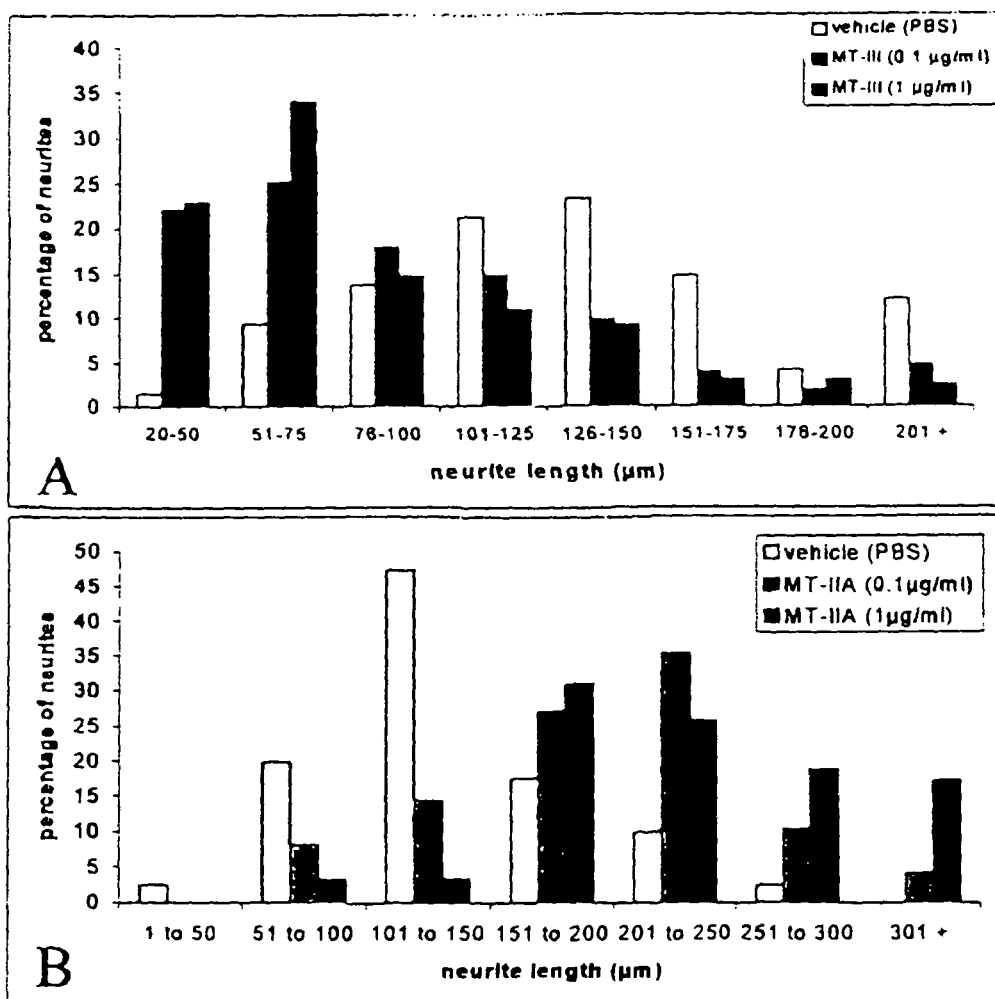
FIG. 8 shows the effect of human MT-III and MT-IIA on the distribution of neurite length of cultured rat cortical neurons.

Turning now to the effect of human MT-III as contrasted to MT-IIA, a series of experiments were conducted as detailed in FIGS. 6 to 12. Referring firstly to FIG. 6, the effect of MT-III on neurite formation is shown in FIG. 6A in the presence of adult rat brain extract at 150 μg/ml after three days. FIG. 6B shows neurite bearing neurons indicated by the arrows. The percentage of neurite bearing neurons is shown in FIG. 6C and the number of neurites per neurite-bearing neuron is shown in FIG. 6D. From the above it can be seen that MT-III significantly inhibits neurite outgrowth in both instances at the concentrations tested (p<0.01, ANOVA). Referring now to FIG. 6E human MT-IIA had no effect on initial neurite outgrowth over three days. As assessed by both the percentage of neurite bearing neurons or as detailed in FIG. 6F, the number of neurites per neurite-bearing neurons. Referring now to FIG. 7, it has been shown that human MT-III prolongs the process of neurite retraction from 0-2 and 2-4 hours after plating as can be seen with reference to FIG. 7A. Following this, the rate of neurite elongation is reduced. Referring now to FIG. 7B, in contrast to this, application with human MT-IIA significantly increases the rate of neurite elongation.

The distribution of neurite lengths three days after MT-III treatment is shown in FIG. 8A, where it is clearly indicated that while MT-III significantly inhibits neurite growth, a small percentage of neurites were unaffected and grew to lengths comparable to vehicle treated neurites. In contrast to this the distribution of neurite lengths following MT-IIA treatment indicated that a number of neurites grew to lengths greater than that of vehicle treated neurites as can be seen with reference to FIG. 8B.

Figure 9A:
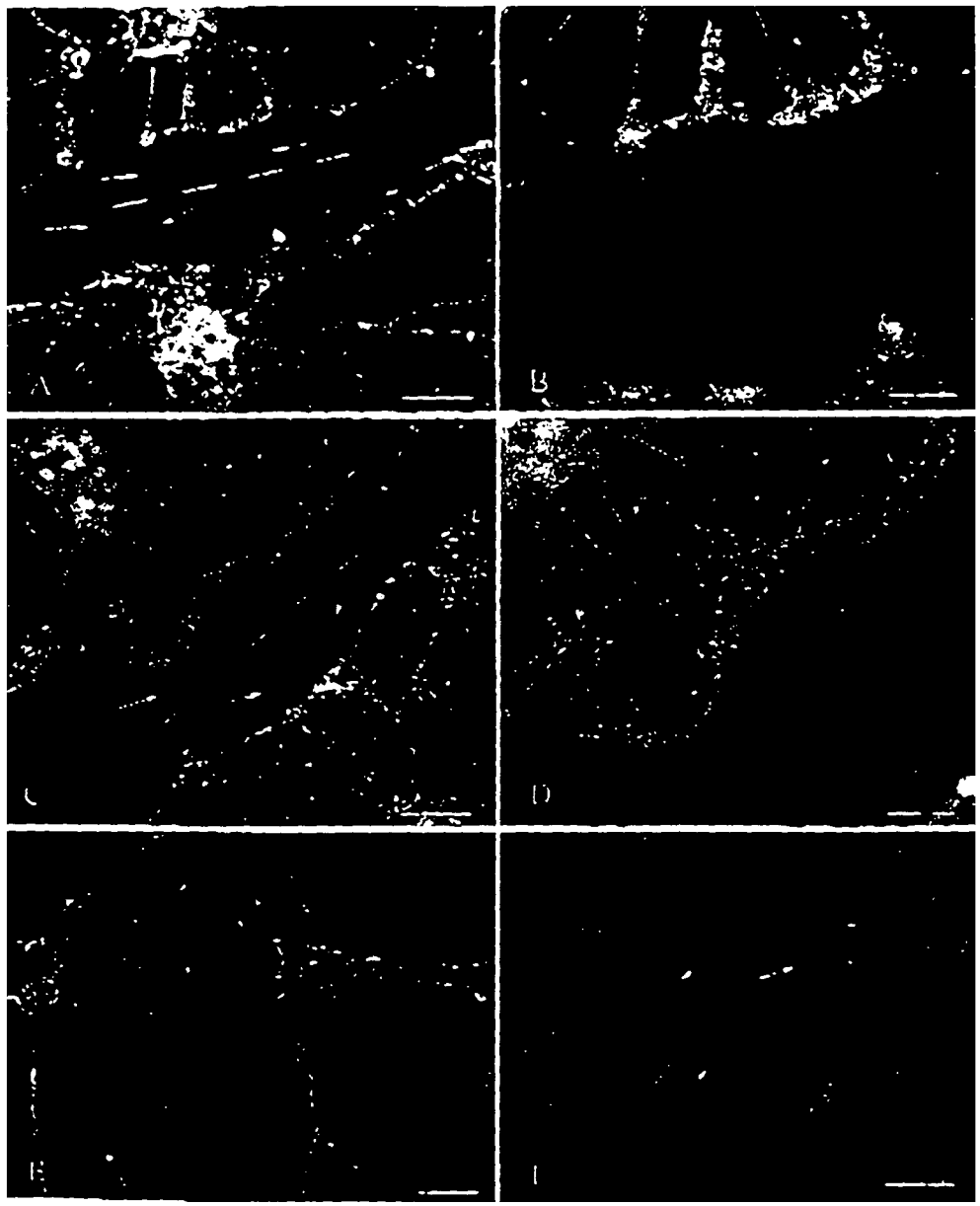
FIG. 9A shows immunocytochemistry the effect of human MT-III and MT-IIA on reactive neurite sprouting.

Fluorescent double immunocytochemical labelling of cytoskeletal changes both tau shown in red and βIII-tubulin shown in green twelve hours after axonal transection are shown in FIGS. 9A Panel A and 9A Panel B. In contrast to this, treatment with MT-III reduced regenerative neurite sprouting compared to vehicle treated samples as shown in FIGS. 9A Panel C and 9A Panel D.

The transection site is indicated by a broken line and there is a large area of retraction away from this line. Sprouting neurites are indicated by arrows. The MT-IIA treatment increased both the number and length of reactive sprouts following injury and this is detailed in FIGS. 9A Panel E which details the vehicle example and 9A Panel F which indicates the MT-IIA example at 1 μg/ml (check, please).

Figure 9B:
FIG. 9B shows by immunocytochemistry the effect of human MT-III and MT-IIA on reactive axonal growth.
Figure 10:
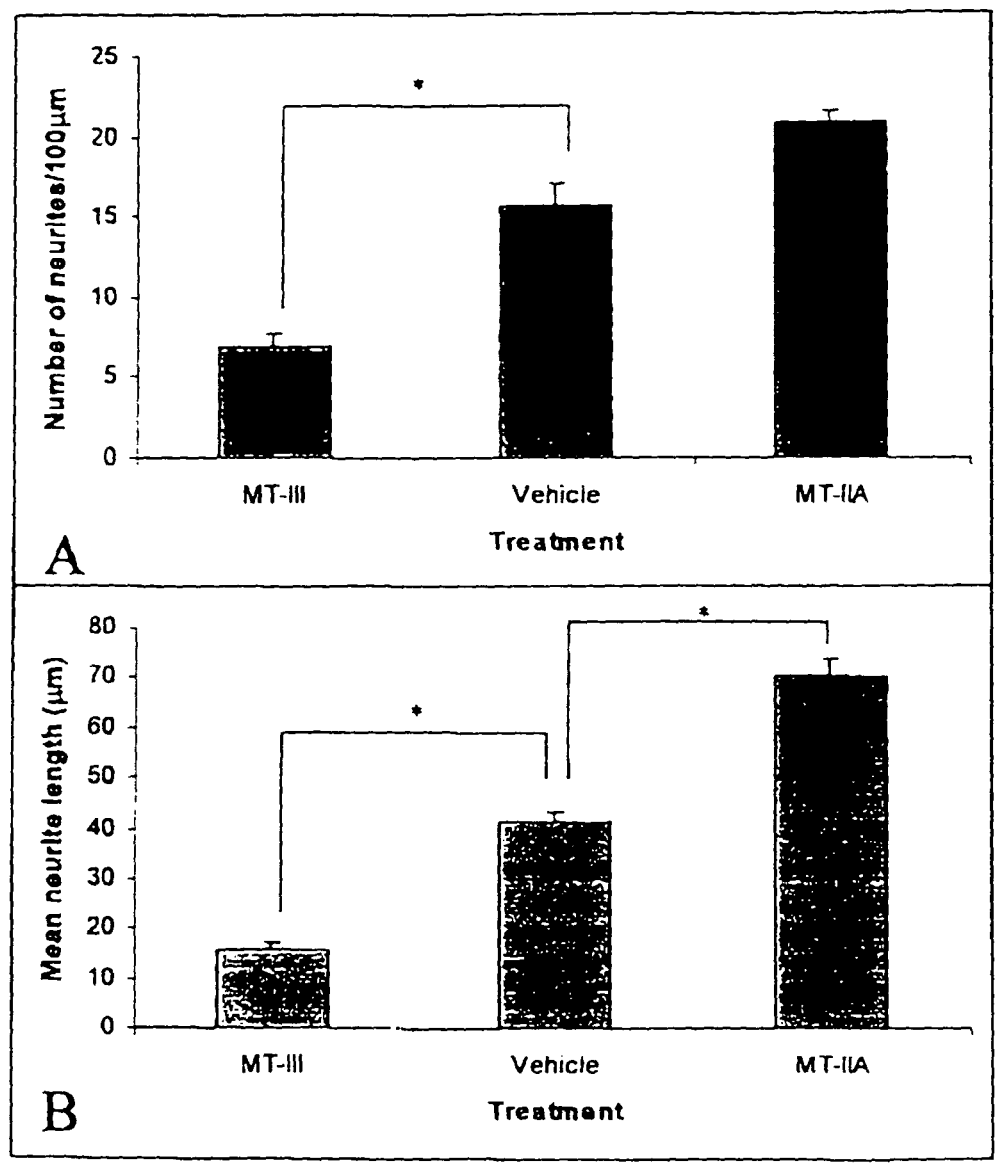
FIG. 10 shows the quantitative effect of human MT-III and MT-IIA on reactive neurite sprouting and growth.

Referring now to the eighteen hours post axonal transection. This is shown by flourescent double immunocytochemcial labelling of cytoskeletal changes, both tau shown in red and βIII-tubulin shown in green. The MT-IIA can be seen to have promoted reactive axonal growth across the entire transection site shown in FIG. 9B Panel A. In contrast such axonal growth is not observed following treatment with either vehicle as shown in FIG. 9B Panel B or MT-III shown in 9B Panel C.

Treatment of samples with human MT-III significantly inhibited both the number and length of reactive sprouts at a twelve hour interval after axonal transection in culture. However, treatment with human MT-IIA significantly increased the mean neurite length of reactive sprouts at 12 hours after transection. These findings are detailed in FIGS. 10A and 10B.

EXAMPLE 3

Figure 11:
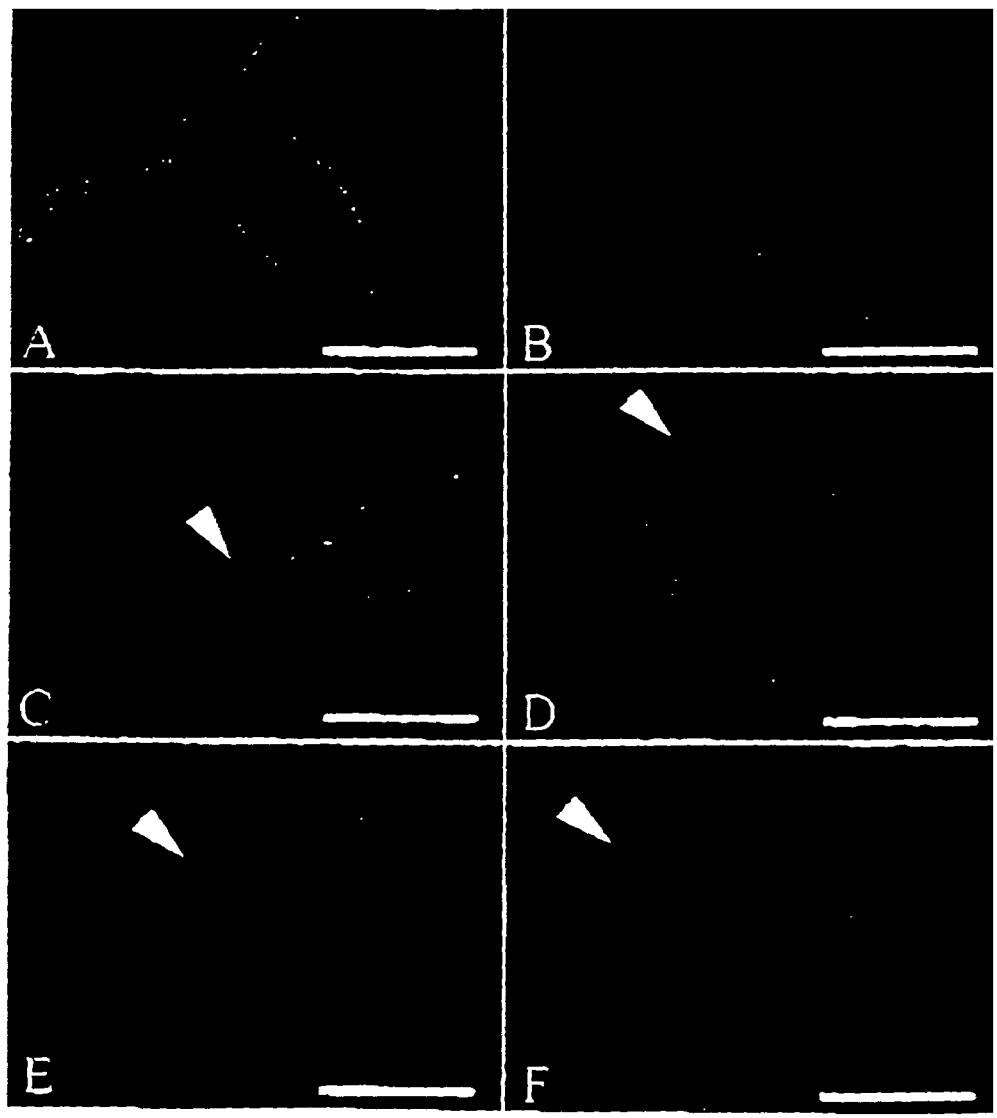
FIG. 11 shows by immunohistochemistry the effect of human MT-IIA on axonal sprouting into a lesion site following physical injury in the rat neocortex.
Figure 12:
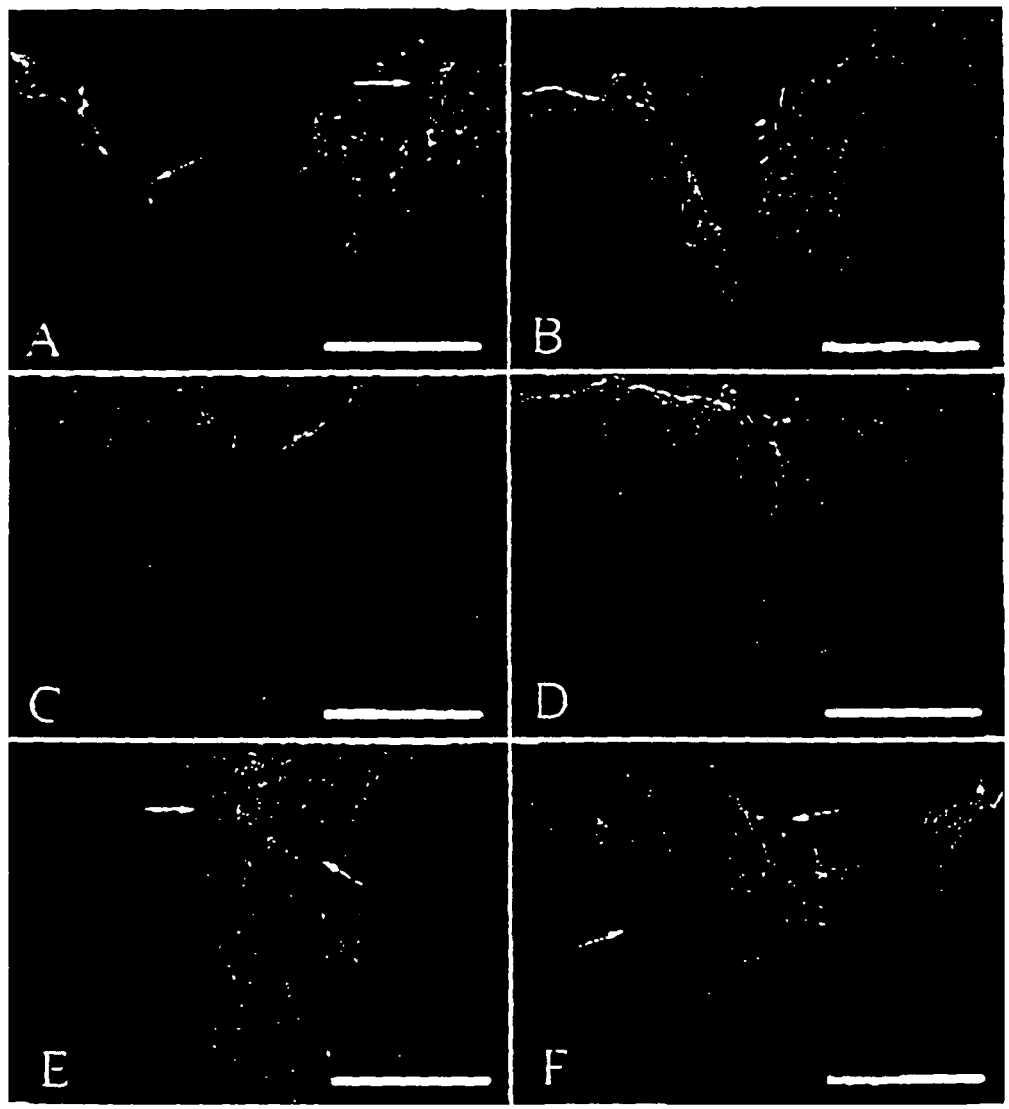
FIG. 12 shows by immunohistochemistry the effect of human MT-IIA on neuronal injury tract repair.

Further experimental work was done to test the effect of MT-IIA and these results are shown in FIGS. 11 and 12 under immunohistochemical studies for SMI-312 (green axonal marker) and ferritin (red microglial marker). Referring firstly to FIG. 11, the results at four days post injury are shown where the needle stick injury resulted in a large injury tract and microglial migration into and surrounding the injury site shown in FIG. 11A. MT-IIA treatment promoted the formation of a tissue bridge enclosing the lesion site from the pial surface down so as to form a tear drop like invagination shown in FIG. 11B. MT-IIA further promoted axonal sprouting into the lesion site at both the pial layer as shown in FIG. 11C and deeper cortical layers shown in FIG. 11D. In contrast to this, very few axonal sprouts were visualised in control rats as shown at the pial level in FIG. 11E and deeper cortical layers as shown in FIG. 11F. The arrow heads indicate the injury tract.

FIG. 12 shows details of further experimental work on brain sections at 7 days post injury. In vehicle treated rats, the injury tract was smaller compared to four days post injury shown in FIG. 11; although it had not completely closed over a degree of reactive sprouting is evident in all animals at this time point as shown in FIG. 12A. Reactive processes exhibited greater SMI-312 reactivity than uninjured neuronal processes in surrounding neural tissue. Reactive astrocytes also aligned along the borders of the injury tract as shown in FIG. 12B. In MT-IIA treated rats, the entire injury tract had closed over, and was demarcated only by a fine line of ferritin immunoreactivity as shown in FIG. 12C. Reactive astrocytes also enclose the injury tract, and were found at lower density in adjacent uninjured tissue shown in FIG. 12D. In MT-IIA treated animals, numerous reactive axonal processes were observed as shown by the arrows within the injury tract at both deeper cortical levels shown in FIG. 12E and pial levels shown in FIG. 12F.

EXAMPLE 4

The current example examined the neuroprotective and/or neuroregenerative properties of exogenous MT-I/II at four weeks after complete transection of the optic nerve in adult rat. Retinal ganglion cell (RGC) survival was assessed in retinal wholemounts using TUJ-1 immunoreactivity. Following intra-vitreal MT-I/II administration, 24% of RGCs survived compared to 8% and 11% survival in transection only and transection+PBS injected controls. Furthermore, RGC axons were visualised by GAP43 immunoreactivity or by DiI labelling. In the optic nerve of transection only and transection+PBS injected animals RGC axons had retracted from the transection site, extending approximately 50-70% of the length of the proximal nerve. For MT-I/II injected animals, RGC axons persisted at the transection site; furthermore, in 5/8 animals, a minority of axons had regenerated across the lesion and extended up to 720 m into the distal nerve. The neuroprotective and neuroregenerative effects of MT-I/-II observed in this extreme injury model suggest that exogenous administration represents a promising therapeutic strategy for central nerve tract repair.

Figure 13:
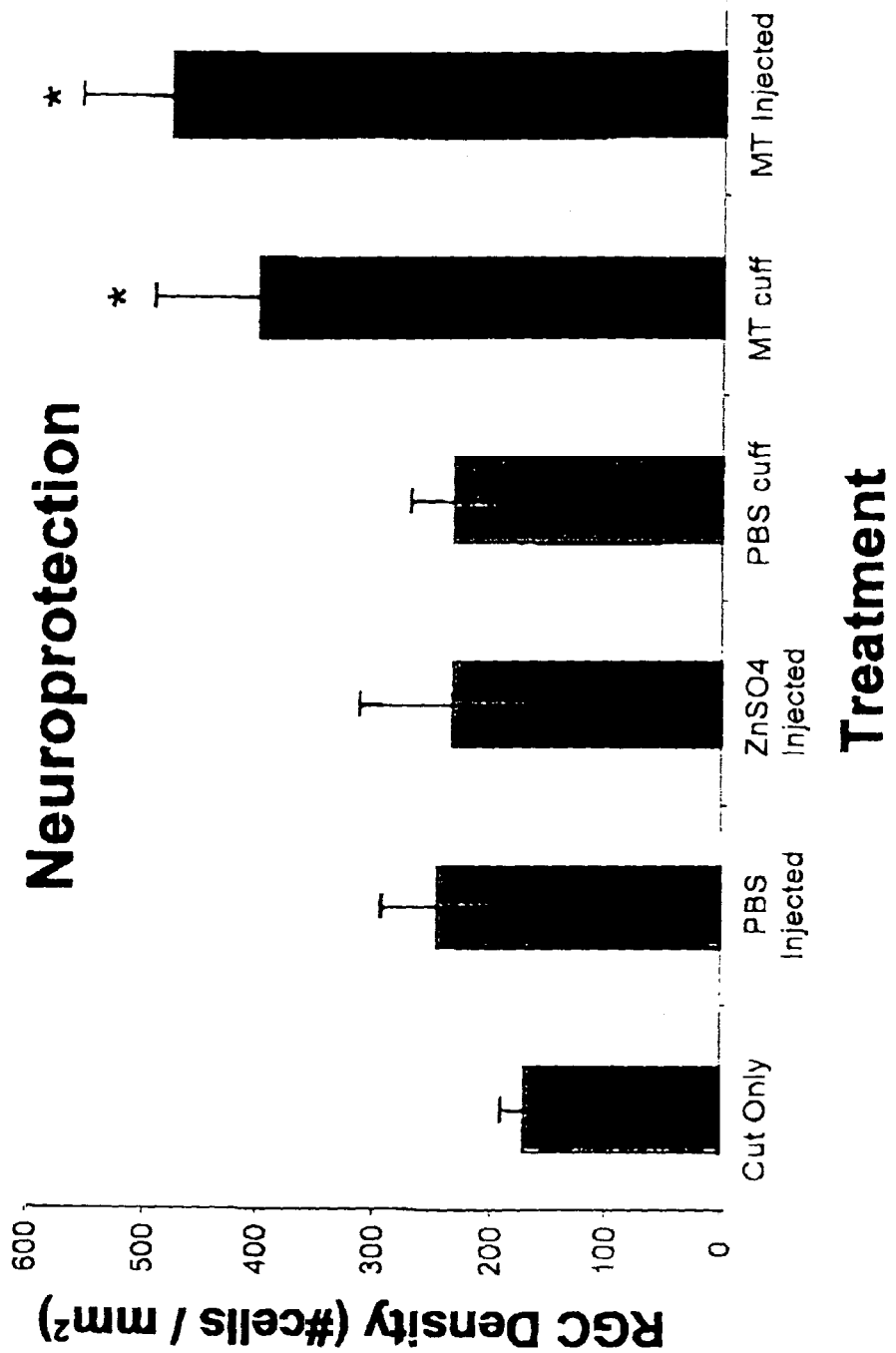
FIG. 13 shows RGC survival following ON transection surgery.

Reference is made to FIGS. 13 to 17 as follows:
FIG. 13

Figure 14:
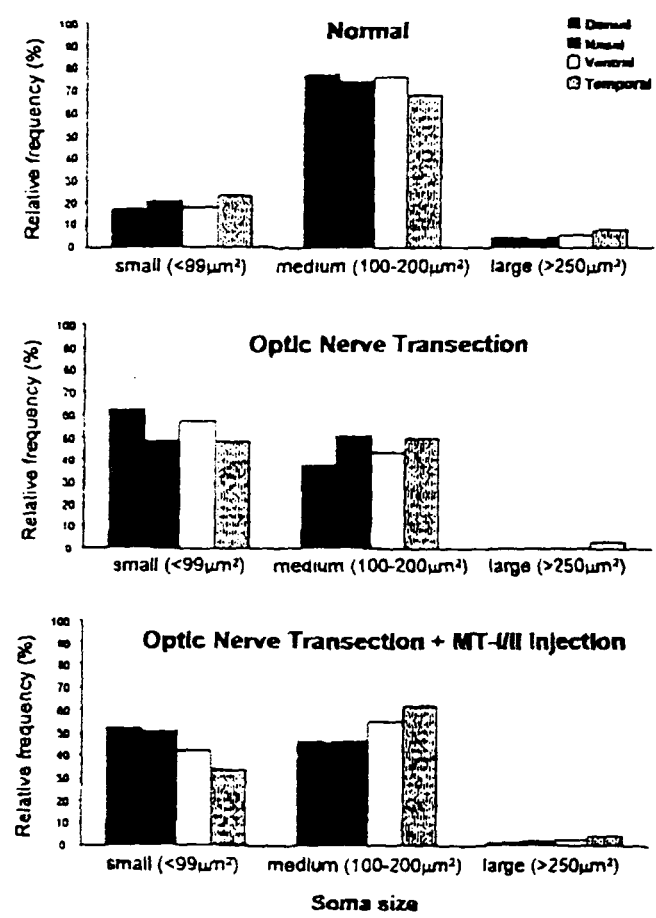
FIG. 14 shows a size frequently histogram of RGCs in retinal whole-mounts.

MT-I/II administration via intravitreal injection and via a gelfoam cuff around the transection site induced significantly greater RGC survival compared with ON transection only animals and PBS/ZnSO4 controls. Increases in RGC survival observed in PBS and $ZnSO_4$ injection, and PBS cuff groups were not statistically significant. Asterisks denote significance (Scheffe Post-hoc test). Results are mean density values±SD.
FIG. 14

Figure 17:
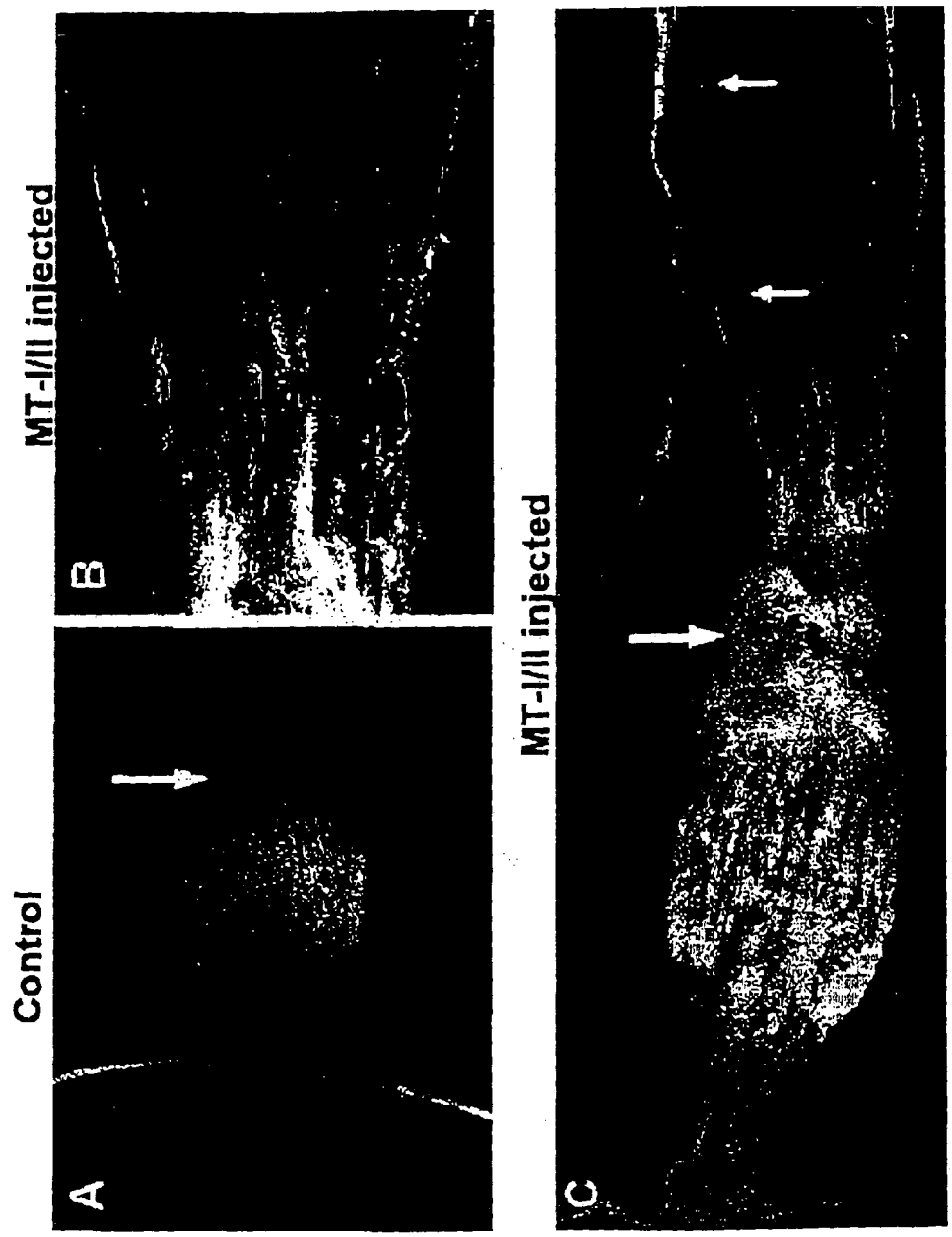
FIG. 17 shows fluorescent images showing DiI labelled RGC axons after ON transection.

Following ON transection, there was a decrease in the number of large RGCs and a relative increase in small RGCs. However, following MT-I/-II administration, medium and large RGCs were more numerous than in the ON cut only group. Data are presented as the prevalence of RGC soma size (%) within each retinal quadrant.
FIG. 17

(A) Confocal image at 4 days after optic nerve transection illustrating abrupt termination of DiI labelled axons at the transection site (large arrow). (B, C) DiI anterograde labelling at 4 weeks after ON transection+MT-I/II injection showing regenerating axons crossing the lesion site (large arrow) and extending into the distal nerve (B). Leading axons extend approximately 1000 μm into the distal nerve (small arrows).
Materials and Methods
Animals and Surgery
Animals Fifty seven adult female PVG hooded rats (180-200 g bw) were used. Surgical anaesthesia involved injections of ilium xylazil-20 6 mg/kg and ketamine 50 mg/kg (i.p.). Terminal anaesthesia was by injection of pentobarbitone (0.1 ml/100 g bw). Procedures conformed to the National Health & Medical Research Council (Australia) Guidelines for the Care and the Use of Experimental Animals and with approval from the Animal Ethics and Experimentation Committee of The University of Western Australia Experimental animals underwent right ON transection with concomitant administration of MT-I/-II (100 ng/l in PBS) to the intravitreal cavity of the right eye (n=4) or to a gelfoam cuff surrounding the transection site (n=6). Control animals underwent either ON transection alone (n=8) or transection+intravitreal injection with either PBS (n=4) or ZnSO4 (n=4; 32 ng/µl), or ON transection+PBS administration to a gelfoam cuff (n=4) around the transection site. In further controls, ONs remained intact but animals received an intravitreal injection of MT-I/-II (n=4) or PBS (n=5). Normal animals were also investigated (n=7).

Surgery

ON Transection

Rats were deeply anaesthetised, the right ON exposed intraorbitally, and the nerve sheath cut transversely except for the ventral aspect that was left intact to avoid damage to the ophthalmic blood vessels. The nerve parenchyma was lifted using hooked forceps and completely transected with iridectomy scissors approximately 1 mm from the back of the eye. The cut ends of the nerve sheath were then sutured together (10-0 thread). The completeness of transection was confirmed by anterograde labelling (see Methods: Tissue Preparation). Any animals with ischaemic retinae (determined ophthalmoscopically) were discarded. Rats were maintained for 4 weeks. Intravitreal injection Intravitreal injections were performed immediately following ON transection. MT-I/-II or control solutions (PBS or ZnSO$_4$) were administered via a stereotactically positioned 30-gauge needle attached to a 10 µl Hamilton syringe. A final volume of 2.5 µl was administered via two injection sites (nasal and temporal).

Gelfoam Cuff

After ON transection a gelfoam cuff soaked in MT-I/II (100 ng/l) or PBS was inserted under the nerve sheath at the transection site. Gelfoam was applied at multiple locations around the nerve to ensure that the injury site was completely encapsulated.

Check for Absence of Toxic Effects

To determine any potential toxic effects of the injected substances we examined non-ON transected animals receiving intravitreal injections of MT-I/II or PBS and compared them to normal animals. Rats were maintained for 4 weeks following intravitreal injection. To label RGCs retrogradely, a crystal of the tracer fluorogold (FG) was applied to the ON approximately 2 mm from the back of the eye 3 days before terminal anaesthesia Non-specific leakage of the tracer beyond the local insertion site was minimal.

Tissue Preparation

Rats were terminally anaesthetized and transcardially perfused with 0.9% sodium chloride followed by 4% paraformaldehyde. The right eye and ON were dissected from the surrounding orbital tissue and post-fixed in 4% paraformaldehyde for 24 hours. Both RGC counts and axon measurements were made within the same animal by separating the retina from the nerve prior to labelling with Tuj1 (retina) or GAP-43 (ON). RGC counts were made from retinal wholemounts; axon measurements from ON sections. Nerves were cryoprotected by immersion in 15% sucrose in PBS overnight. Horizontal serial sections (16 m) were collected onto Superfrost® Plus glass slides and stored at −70° C.

Anterograde DiI (1,1-dioctadecyl-3,3,3',3'-tetramethylindocarbocyanine perchlorate) tracing was performed on 2 groups of rats: MT-I/II injected ON transected animals that survived for 4 weeks (n=6) and animals that had undergone ON transection and survived for 4 days only, to verify the completeness of transection (n=3). Crystals of DiI were placed on the ON head and allowed to transport in a 37° C. incubator for 4 weeks. Nerves were then sectioned horizontally at 120 m using a Vibratome. Anxons were traced by confocal microscopy (Biorad). Labelling of optic nerves at 4 days after transection demonstrated that RGC axons did not extend beyond the site of transection, confirming the completeness of surgery (FIG. 17A).

Immunohistochemistry

Retinae were incubated with Tuj-1 (βIII microtubulin) primary antibody diluted 1:500 with PBS+0.2% tritonX100 in a humid chamber overnight at 4° C. Antibody binding was visualised following incubation (2 hours) with anti-mouse (1:400, Alexa 488, Molecular Probes) secondary antibody. Retinae were wholemounted onto glass slides, coverslipped using Fluoromount G and viewed using a conventional fluorescence microscope. ON sections were air-dried for 1-2 hours at room temperature prior to use. Tissue was re-hydrated in PBS+0.2% triton X100 for 10 minutes, followed by overnight incubation with an antibody to growth associated protein (GAP43, rabbit polyclonal 1:500. Binding was visualised with an anti-rabbit (1:400, Alexa 546, Molecular Probes) secondary. GAP43 labelling was viewed using conventional fluorescence microscopy.

Analysis

RGC Counts

RGCs labelled with FG (BP 340-380 excitation filter) and TUJ1 (BP 450-490 filter) were counted in 24 representative, non-overlapping rectangular sample fields of 191.16 µm×257.14 µm (6 fields in each retinal quadrant; 3 retinal eccentricities, ⅙, ½ and ⅚ of the retinal radius). Each sample area was photographed at a final magnification of 250× using a digital camera. Manual cell counts were made using ImagePro® image analysis software. The total number of labelled RGCs per retina was calculated by multiplying the mean cell number per sample area by the area of the retina. Counts were made whilst blind to the treatment group.

RGC Sizes

RGC soma area was calculated for normal animals, ON transection only animals and ON transection+intravitreal MT-I/II. Two hundred cells were analysed per retina, similar to the procedure of Vidal-Sanz et al. (1987). RGCs were analysed in sample frames taken from peripheral retina only, since cell size within classes has been shown to vary with retinal eccentricity. Fifty cells each from dorsal, nasal, ventral and temporal retina were manually traced and the soma area computed. RGCs were allocated to one of three broad groups based on their area: small (<99 µm$^2$), medium (100-250 µm$^2$) and large (>250 µm$^2$).

Axon Measurements

The transected ON was analysed as segments proximal and distal to the lesion. For the proximal segment, the distance from the ON head to the point at which GAP43-positive RGC axons terminated was measured and expressed as a percentage of the length of the proximal nerve. For the distal nerve segment the distance that regenerated RGC axons projected beyond the transection site was measured and is presented as raw data RGC axons were photographed at a final magnification of 250× and distances measured using a calibrated measurement tool. Analyses were performed only on ON sections in which the nerve head, proximal nerve, transection site and distal nerve were visible.

RGC counts and axon measurements were analysed using ANOVA (StatView) and p values calculated using the Scheffe post hoc test.

Results
RGC Counts

In normals, there was an almost 100% correlation between FG tracing and TUJ1 labelling (not shown), supporting the use of TUJ1 as a specific marker for RGCs.

Intravitreal Injection

The average RGC density for normal animals was 2145+179 cells/mm$^2$, equivalent to a total population of 114,032. Intravitreal injection of MT-I/-II or PBS in animals with intact ONs did not significantly alter (p>0.05) RGC survival (MT-I/II: 1962+70 RGCs/mm$^2$; PBS: 1966+18 RGCs/mm$^2$). Indeed the distribution and morphology of RGCs was indistinguishable between animals receiving MT-I/-II or PBS and normals.

At 4 weeks following ON transection alone, RGC numbers had decreased to 170+20 RGCs/mm$^2$, equivalent to 8% of the normal population (FIG. 13). Values were not significantly different (p>0.05) from ON transection animals with PBS-injection (244+49 RGCs/mm$^2$) or ZnSO$_4$-injection (245+85 RGCs/mm$^2$).

Intravitreal MT-I/-II administration produced a significant increase (p<0.05) in RGC survival with an average of 483+76 RGCs/mm$^2$. This value is equivalent to 24% of the normal RGC population or 27,200 RGCs in total.

Gelfoam Cuff

RGC survival following PBS administration to a gelfoam cuff surrounding the transection site was 233+39 RGCs/mm$^2$. This was similar to the result for intravitreal PBS administration and, again, was not significantly different (p>0.05) from survival in ON transection only animals. However, MT-I/II administration via a gelfoam cuff resulted in a significant increase in survival compared to ON transection only and PBS cuff animals (p<0.05) with 404+91 RGCs/mm$^2$. The value is equivalent to 19% of the normal RGC population.

RGC Sizes

Across the three groups: normals, ON transection only and ON transection+MT-I/II injection, RGC sizes ranged from 54 μm$^2$-486 μm$^2$ in area In normal rats, approximately 75% of RGCs were medium sized (soma area 100-250 μm$^2$), 20% were small (area<99 μm$^2$) and 5% large (>250 μm$^2$). After ON transection, there was a marked increase in the prevalence of small RGCs, and a selective loss or atrophy of large and medium sized RGCs within the surviving population. Following intravitreal MT-I/-II administration, smaller cells were again more prevalent relative to normal animals, however the decrease in large and medium sized cells was less severe than in the ON transection only group.

Axon Measurement

Figure 15:
FIG. 15 shows GAP43 labelled axons in the proximal optic nerve of PBS and MT-I/II injected animals at 4 weeks after optic nerve transection surgery. Arrows indicate site of transection.
Figure 15:
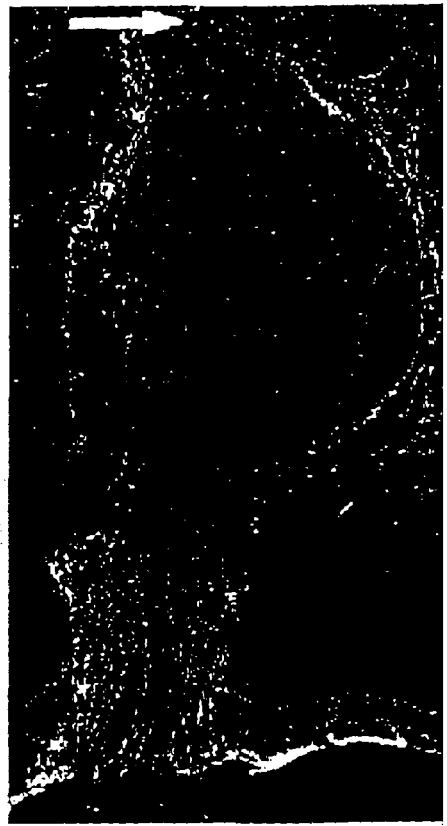
Figure 16:
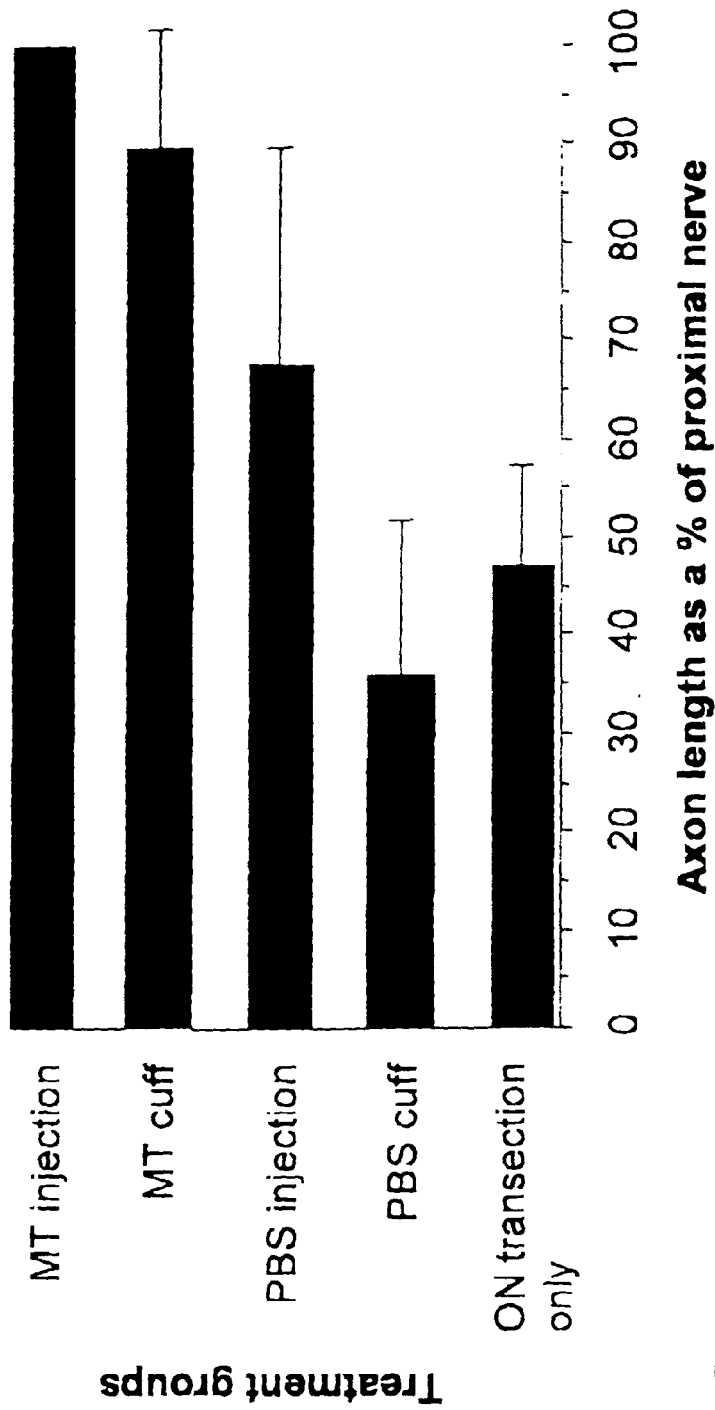
FIG. 16 shows location of RGC axons within the proximal nerve 4 weeks after ON transection.

Qualitatively, GAP43-labelled RGC axons at 4 weeks after ON transection only or ON transection+PBS injection, demonstrated degenerative morphology (FIG. 15). Axons were sparsely arranged within the nerve, had retracted from the transection site and exhibited punctate labelling. By contrast, axons in animals undergoing ON transection+MT-I/II injection not only retained their positions at the transection site, but the proximal nerve was open observed to swell, becoming engorged with axons. Quantitatively, axons in the ON transection only group extended 47+10% of the length of the proximal nerve, ON transection+PBS injected animals projected 67+23%, whereas axons in MT-I/II injected animals extended significantly further (p<0.05) remaining at 100+0% of the proximal nerve (ie. at the transection site; FIG. 4).

Moreover, animals in the ON transection only or PBS injection+ON transection groups consistently lacked GAP43-labelled axons beyond the transection site. However, five out of eight animals with intravitreal MT-I/II administration demonstrated axons projecting an average of 346+288 m past the site-of ON transection, with the most successful axons extending 720 m. The result was confirmed with DiI tracing, in which axons were observed up to 1000 m beyond the site of optic nerve transection (FIG. 17B, C).

This example shows that a single administration of exogenous MT-I/-II following complete optic nerve (ON) transection in adult rat has profound neuroprotective and neuroregenerative properties. The protein rescues a substantial proportion of axotomised RGCs from death, as well as stimulating RGC axon regeneration across the site of transection into the distal nerve.

MT Action

Twenty-four percent of the total RGC population survived 4 weeks after ON transection when animals were injected intravitreally with MT-I/-II, compared to 8% survival in ON transection only controls. The result is consistent with previous studies indicating that MT-I/-II is neuroprotective following a variety of physical and chemical insults. For example, transgenic mice lacking MT-I/-II recover poorly from various types of brain injury including cortical cryolesion and focal cerebral ischemia. Conversely, MT-I/-II over-expression leads to clinical improvement in experimental autoimmune encephalomyelitis, and improves recovery from cortical damage caused by over-expression of inflammatory cytokines.

The molecular mechanisms underlying MT-induced neuroprotection are not yet understood. Suggestions include the ability of MTs to scavenge free radicals and modulate the inflammatory response. MT-I/-II null mice have a prolonged and impaired inflammatory response to injury. Whereas exogenous MT has been shown to modulate the immune response following cortical cryolesion and experimental autoimmune encephalomyelitis. Alternatively, it has been suggested that the protective effect of MT-I/-II relates to its ability to inhibit apoptosis by interacting with the anti-apoptotic transcription factor, nuclear factor kappa B. Indeed, mice lacking MT-I/-II show increased susceptibility to apoptosis compared to wild type mice.

Other studies suggest that the protective action of MT is effected by altering zinc or copper homeostasis, assisting the action of antioxidants such as superoxide dismustase. Furthermore, zinc has also been shown to interact with other enzymes and proteins, including transcription factors, that contribute to inhibition of apoptosis. We have demonstrated that, following ON transection, the neuroprotective action of MT-I/II is not a function of its regulation of the bio-availability of zinc. Indeed, RGC survival in the presence of ZnSO$_4$ was similar to that following PBS administration and was not significantly elevated compared to controls.

Transection of the ON and sheath 1 mm behind the eye and in the absence of a facilitatory peripheral nerve graft or neurotrophic factors, represents one of the most severe and intractable injury paradigms. Nevertheless, immnunohistochemical and anterograde axon tracing studies revealed that MT-I/-II supports RGC axon regeneration across the lesion site and into the distal nerve. By contrast, RGC axons in control animals had retracted from the vicinity of the transection site, filling only 50-70% of the proximal nerve. The result highlights the regenerative potential of MT-I/-II, indicating that an even more favourable outcome might be expected under less severe conditions such as nerve crush. The mechanism by which MT-I/II exerts its neuroregenerative action is unknown. However, the differential response we observed for the application of MT-I/II intravitreally or to the site of ON transection indicates that the protein is likely to operate directly on the nerve cell body.

Comparison of MT with Other Neuroprotective Agents

Survival of adult rat RGCs was promoted by a single intravitreal injection of inosine (a purine derivative) after ON transection. Inosine rescued 25% of the normal RGC population 2 weeks after injury. Although the results indicate a similar extent of RGC survival to that reported here (24% survival), the ON transected controls demonstrated a surprisingly high level of survival at 19% indicating that protection was only 1.3 fold greater than controls. By contrast, in the present study, ON transected controls exhibited only 8% RGC survival, matching previous reports and representing a 3 fold increase in survival. Two other aspects differ between the studies and argue a possibly greater efficacy for MT-I/II. RGC survival was examined at a later time point (4 weeks compared to 2 weeks), during which time many RGCs would die after simple axotomy. The ON was transected closer to the back of the eye (1 mm compared with 1.5 mm), a location leading to a more rapid onset of RGC death compared to more distal surgery It is possible that MT-I/-II would yield greater neuroprotection and neuroregeneration if it were injected more frequently than the single application performed in the current study. For example, multiple applications of macrophage inhibitory factor (MIF) increased RGC neuroprotection at four weeks after ON transection in adult rat to 37% compared to 17% after a single dose.

Other studies have noted modest protection of RGCs after ON transection. In recent studies examining RGC survival 2 weeks after ON transection, intravitreal administration of erythropoietin at 0, 3, 7 and 10 days produced a 0.9 fold increase in survival compared to controls, whereas the antibacterial drug Rifampicin was found to produce a 0.6 fold increase in survival in ON transected mice. The results are lower than the 3 fold increase demonstrated following MT administration in the current study.

Comparison of MT with Other Neuroregenerative Agents

The extent of RGC axon regeneration stimulated by MT-I/II after transecting the adult rat ON suggests that the protein is one of the most potent of reported neuroregenerative factors. The applicant did not estimate the proportion of RGC axons that regenerated beyond the lesion site due to inherent inaccuracy in quantifying axon numbers, as regenerating axons may follow contorted paths and may bifurcate or even trifurcate. Nevertheless, the regeneration appears similar in extent (see FIG. 3) to a recent study in which RGCs growth-sensitised by lens injury were transfected with adeno-associated viruses carrying a gene for C3 ribosyltransferase to inactivate Rho-A. Transfecting growth-sensitized RGCs with adeno-associated viruses expressing a dominant-negative form of NgR (NgR(DN)) also increased axon regeneration several-fold; however, when the growth program of RGCs was not activated, NgR(DN) expression lacked beneficial effects.

Studies by Leon et al., (2000) and Yin et al., (2003), increased numbers of activated macrophages within the eye following lens injury and zymosan injection, respectively. Lens injury was found to result in around 200 axons extending 1 mm beyond the ON crush site 2 weeks after injury, whereas zymosan produced 500 axons extending 1 mm beyond the crush site after 2 weeks, with the most successful axons extending 4-5 mm. Similarly, Berry et al., (1996) reported RGC axons regenerating 3-4 mm when a segment of peripheral nerve was implanted within the eye. Although in both instances regeneration appears superior to that induced by MT-I/-II (maximum axon regrowth of ≈0.75 mm), the studies employed a less severe injury model, ON crush rather than transection and were performed at a greater distance (2 mm) from the posterior pole of the eye. Modest regeneration has been reported following treatment with group B-streptococcus exotoxin leading to macrophage stimulation, increased phagocytosis of inhibitory debris, and a less dense reactive gliosis, which in turn allows for regrowth of axons through the glial scar.

RGC axons more readily regenerate into a peripheral nerve graft an effect enhanced by the synergistic effects of increased cAMP levels or of Nogo-neutralizing antibody IN-1 along with ciliary neurotrophic factor. Similarly, brain derived neurotrophic factor (BDNF) induced RGC axon regeneration into autologous connective tissue chambers implanted into a gap-injury site in the adult rat optic nerve.

The above detailed examples demonstrate the clinical application of MT-IIA in promoting nerve cell survival, promoting neuronal regeneration and generally enhancing neurite elongation without causing inappropriate neuronal sprouting.

The findings and experimental results support many clinical applications of the invention as detailed below.

| Disease | Indication | Role of MTI/II (IIA) |
|---|---|---|
| Alzheimer's disease | Promote nerve cell survival. Promote neuronal regeneration. Buffer metals implicated in development of pathological hallmarks. | It was demonstrated that MTI/II is upregulated in early stages of the disease (published) |
| Parkinson's disease Promote nerve cell survival. Promote regeneration. | Buffer metals implicated in toxicity. Evidence of abnormal metal homeostasis in the brain as well as neurodegeneration. | |
| Motor neuron disease | Promote nerve cell survival. Promote neuronal regeneration. Buffer metals implicated in toxicity. Reduce oxidative stress implicated in neuronal degeneration. | Evidence of abnormal metal homeostasis in the brain and spinal cord as well as neurodegeneration. |
| Head injury | Promote nerve cell survival. Promote neuronal regeneration. | It was shown that MT I/II is upregulated at zone of injury. Recombinant protein promotes brain healing and axonal regeneration |

-continued

| Disease | Indication | Role of MTI/II (IIA) |
|---|---|---|
| Spinal cord trauma | Promote nerve cell survival. Promote neuronal regeneration. | Evidence of delayed neurodegeneration and spinal cavitation following injury. The recombinant protein is potentially capable of promoting neural healing and regeneration. |
| Glaucoma | Promote nerve cell survival. Promote neuronal regeneration. | Axonal damage followed by neurodegeneration underlies the disease. MTI/II may potentially promote survival of nerve cells and/or appropriate regeneration. |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of stimulating outgrowth of neurites comprising:
contacting a target living neuron or live neuronal area with a solution of a metallothionein isoform selected from the group consisting of MT-I, MT-II and synthetic forms thereof so as to deliver a sufficient amount of said metallothionein to stimulate said outgrowth of neurites; and measuring neurite growth after contacting with the solution.

2. A method according to claim 1 wherein said MT-II is human MT-IIA.

3. A method according to claim 2 wherein said MT-II is recombinant human MT-IIA.

4. A method according to claim 1 wherein said solution has a concentration of up to about 5 µg/ml metallothionein in a neurologically acceptable carrier.

5. A method according to claim 4 wherein said solution has a concentration of about 5 µg/ml metallothionein in solution.

6. A method according to claim 1 further comprising exposing said neuron or neuronal area to at least one additional metallothionein isoform or a combination of metallothionein isoforms selected from the group consisting of MT-I, MT-II, MT-III and MT-IV.

7. A method according to claim 6 wherein said target neuron or neuronal area is exposed simultaneously to a combination of MT-IIA and any one or a combination of metallothionein isoforms selected from the group consisting of MT-I, MT-II, MT-III and MT-IV.

8. A method according to claim 6 wherein said target neuron or neuronal area is exposed sequentially to a combination of MT-IIA followed by any one or a combination of metallothionein isoforms selected from the group consisting of MT-I, MT-II, MT-III and MT-IV.

9. A method according to claim 6 wherein said target neuron or neuronal area is exposed sequentially to MT-I or MT-II and then to another metallothionein isoform selected from the group consisting of MT-I, MT-II, MT-IIA, MT-III, and MT-IV.

10. A method according to claim 1 wherein said neuron or neuronal area is located in the brain.

11. A method according to claim 1 wherein said solution is administered to said neuron or neuronal area by direct injection.

12. A method of treatment of Alzheimer's Disease comprising administration to a patient in need of treatment a therapeutic composition including metallothionein in accordance with the method of claim 1.

13. A method of treatment of Parkinson's Disease comprising administration to a patient in need of treatment a therapeutic composition including metallothionein in accordance with the method of claim 1.

14. A method of treatment of motor neuron disease comprising administration to a patient in need of treatment a therapeutic composition including metallothionein in accordance with the method of claim 1.

15. A method of treatment of head injury comprising administration to a patient in need of treatment a therapeutic composition including metallothionein in accordance with the method of claim 1.

16. The method of claim 1, wherein the solution is applied directly to exposed neurons.

17. A method of stimulating outgrowth of neurites comprising directly contacting a target living neuron or live neuronal area with a solution of a metallothionein isoform selected from the group consisting of MT-I, MT-II and synthetic forms thereof so as to deliver a sufficient amount of said metallothionein to stimulate said outgrowth of neuritis; and measuring neurite growth after contacting with the solution.

18. A method of treatment of Alzheimer's Disease comprising administration to a patient in need of treatment a therapeutic composition including metallothionein in accordance with the method of claim 17.

19. A method of treatment of Parkinson's Disease comprising administration to a patient in need of treatment a therapeutic composition including metallothionein in accordance with the method of claim 17.

20. A method of treatment of motor neuron disease comprising administration to a patient in need of treatment a therapeutic composition including metallothionein in accordance with the method of claim 17.

21. A method of treatment of head injury comprising administration to a patient in need of treatment a therapeutic composition including metallothionein in accordance with the method of claim 17.

* * * * *